United States Patent
Quint

(10) Patent No.: US 10,709,554 B2
(45) Date of Patent: Jul. 14, 2020

(54) HEART VALVE PROSTHESIS FOR CONTROLLED THROMBUS DEVELOPMENT

(71) Applicant: BIOTRONIK AG, Buelach (CH)

(72) Inventor: Bodo Quint, Dettighofen (DE)

(73) Assignee: BIOTRONIK AG, Buelach (CH)

( * ) Notice: Subject to any disclaimer, the term of this patent is extended or adjusted under 35 U.S.C. 154(b) by 0 days.

(21) Appl. No.: 15/446,381

(22) Filed: Mar. 1, 2017

(65) Prior Publication Data
US 2017/0252155 A1  Sep. 7, 2017

(30) Foreign Application Priority Data
Mar. 3, 2016  (DE) .......................... 10 2016 103 843

(51) Int. Cl.
*A61F 2/24* (2006.01)
*A61L 27/26* (2006.01)

(52) U.S. Cl.
CPC .............. *A61F 2/2418* (2013.01); *A61F 2/24* (2013.01); *A61F 2/246* (2013.01); *A61L 27/26* (2013.01); *A61F 2250/0067* (2013.01); *A61F 2250/0069* (2013.01); *A61L 2400/04* (2013.01); *A61L 2430/20* (2013.01)

(58) Field of Classification Search
CPC ........ A61F 2/24; A61F 2/2412; A61F 2/2415; A61F 2/2418
See application file for complete search history.

(56) References Cited

U.S. PATENT DOCUMENTS

| | | | |
|---|---|---|---|
| 4,374,175 A * | 2/1983 | Tanaka ................. | A61C 9/0033 428/369 |
| 6,306,176 B1 * | 10/2001 | Whitbourne .......... | A61L 29/085 427/2.24 |
| 7,717,952 B2 | 5/2010 | Case et al. | |
| 2005/0240137 A1 | 10/2005 | Zhu et al. | |
| 2006/0013863 A1 | 1/2006 | Shalaby et al. | |
| 2006/0047338 A1 * | 3/2006 | Jenson ................... | A61F 2/2412 623/2.11 |
| 2008/0033522 A1 * | 2/2008 | Grewe .................. | A61L 31/082 623/1.11 |
| 2009/0030504 A1 * | 1/2009 | Weber ................... | A61L 31/022 623/1.42 |
| 2010/0324664 A1 * | 12/2010 | Holzer ................... | A61F 2/856 623/1.35 |

(Continued)

FOREIGN PATENT DOCUMENTS

| | | |
|---|---|---|
| DE | 20 2008 018 551 U1 | 12/2015 |
| WO | 2014144937 A2 | 9/2014 |
| WO | 2015175450 A1 | 11/2015 |

OTHER PUBLICATIONS

Prechtel, A. "European Search Report", EP application 17157885.9, dated Jul. 27, 2017, 7 pages.

(Continued)

*Primary Examiner* — Jason-Dennis N Stewart
(74) *Attorney, Agent, or Firm* — Greer, Burns & Crain, Ltd; Steven P. Fallon

(57) ABSTRACT

The invention relates to a heart valve prosthesis including a heart valve a main body for supporting the heart valve. The heart valve includes a terminating material selected from material and configured to at least partially close a paravalvular leak by controlled thrombus development.

27 Claims, 3 Drawing Sheets

(56) References Cited

U.S. PATENT DOCUMENTS

| | | | |
|---|---|---|---|
| 2011/0217388 A1* | 9/2011 | Greenspan | A61L 27/24 |
| | | | 424/602 |
| 2012/0203326 A1* | 8/2012 | Montenegro | A61L 31/042 |
| | | | 623/1.15 |
| 2013/0150957 A1* | 6/2013 | Weber | A61F 2/2412 |
| | | | 623/2.15 |
| 2014/0277424 A1 | 9/2014 | Oslund | |
| 2014/0350668 A1* | 11/2014 | Delaloye | A61F 2/2418 |
| | | | 623/2.17 |
| 2015/0148889 A1 | 5/2015 | Angel et al. | |
| 2016/0022444 A1 | 1/2016 | Delaloye et al. | |
| 2016/0030521 A1 | 2/2016 | Chilkoti | |
| 2016/0038280 A1 | 2/2016 | Morriss et al. | |

OTHER PUBLICATIONS

Hoeckenreiner, Hans, "German Search Report", German Patent Application No. DE 10 2016 103 843.1, dated Nov. 4, 2016, 9 pages.

\* cited by examiner

HEART VALVE PROSTHESIS FOR CONTROLLED THROMBUS DEVELOPMENT

PRIORITY CLAIM

This application claims priority under 35 U.S.C. § 119 and all applicable statutes and treaties from prior German Application DE 10 2016 103 843.1, filed Mar. 3, 2016.

TECHNICAL FIELD

The present invention relates to a heart valve prosthesis comprising a device for controlled thrombus development.

BACKGROUND

A heart valve prosthesis of this type includes a heart valve, which is intended to replace a heart valve in the patient, and also a main body (generally in the form of a stent), which serves to support the replacement heart valve, wherein the replacement heart valve is secured to the main body.

Such prostheses are used for example within the scope of transcatheter aortic valve implantation (TAVI). Here, paravalvular leaks, where the blood flows through between the vessel wall and the inserted prosthesis, constitute one of the most serious complications and limit the procedural efficacy of minimally invasive heart valves.

On this basis, the object of the present invention is to provide a heart valve prosthesis which counteracts the risk of a paravalvular leak.

SUMMARY

A preferred embodiment heart valve prosthesis includes a heart valve and a main body for supporting the heart valve. The heart valve is secured to the main body. The heart valve prosthesis includes a terminating material on an outer side of the main body selected of a material and configured to induces a thrombus. The terminating material is a preferably a liquid permeable material. The terminating material is preferably a polymer, a biological polymer, an artificial polymer, a cationic polymer, a polycation, or chitosan.

The terminating material can include plurality of fibres, and preferably multi-filaments, including in each case a plurality of interconnected fibres. The fibres or the multi-filaments can be secured to the main body in an integrally bonded, force-fitting and/or form-fitting manner. The individual fibres can be configured and of material such that, in the event of contact with water, to deform from an elongate first state into a second state, wherein the fibres in the second state have a multiplicity of curvatures. The fibres can include a polymer mixture, such as a chitosan and a water-insoluble polymer, preferably P(VP-co-VAc). The fibres can be coated, preferably with a soluble polymer. The soluble polymer can be selected from the group comprising or consisting of polyvinylpyrrolidone, polyethylene glycol, hyaluronic acid, and polysugars, in particular pullulan or dextrans The terminating material in a preferred embodiment is arranged in a blood-permeable bag, which is arranged on the outer side of the main body and is secured to the main body. In preferred embodiments, the bag includes at least one of the following materials or consists of at least one of the following materials: polyethylene, polyethylene terephthalate, polyethylene succinate, polybutylene succinate, polyester, polylactide, polycaprolactone.

BRIEF DESCRIPTION OF THE DRAWINGS

Further features and advantages of the invention will be described hereinafter on the basis of the description of the drawings illustrating embodiments of the invention, in which.

Figure 1:
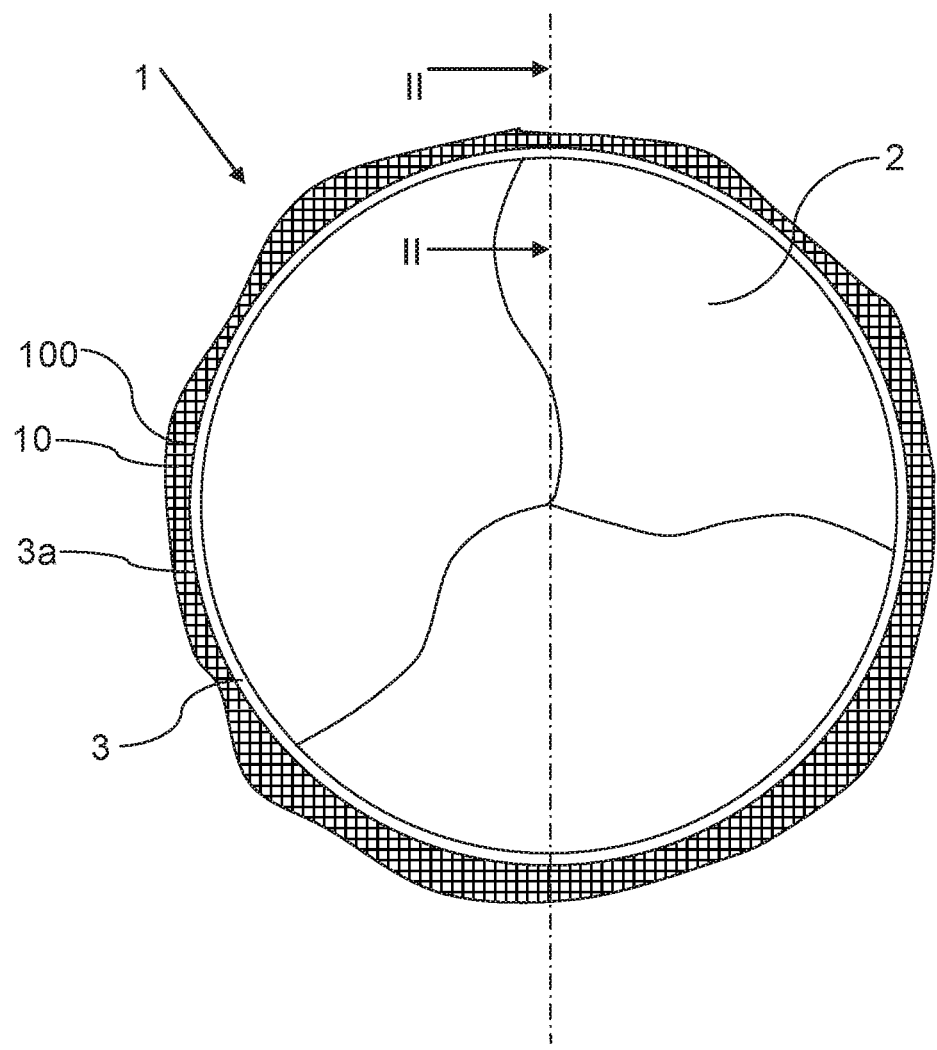
FIG. 1 shows a schematic plan view of a heart valve prosthesis according to the invention in the embodiment with a bag for receiving a terminating material.

A heart valve prosthesis is provided, by preferred embodiments, in the form of a heart valve which preferably is an artificial heart valve formed from a biological tissue, and having a main body for supporting the heart valve, wherein the heart valve is secured to the main body, wherein the heart valve is preferably sewn to the main body. In accordance with the invention, provision is now made so that the heart valve prosthesis has a liquid-permeable terminating material on an outer side of the main body for avoiding a paravalvular leak of the heart valve prosthesis, which material is designed to produce a thrombus in the event of contact with the patient's blood, which thrombus closes or seals off a paravalvular leak at least in part, preferably completely. The terminating material is formed here preferably as fibre material, which is characterised here in that it includes a multiplicity of fibres. The terminating material, however, can also be provided for example in the form of a liquid-permeable sponge-like structure, at which a thrombus forms in a controlled manner after insertion of the heart valve prosthesis into the patient.

In other words, the invention thus relates to a mechanism for producing a systematic volume gain of natural sealing material as a result of thrombus formation and in particular also a spatial limitation thereof. Gaps via which paravalvular leaks would otherwise occur can thus be closed without the volume of sealing material necessary for this purpose having to be delivered systematically as part of the implant. This has the significant advantage, in particular with regard to the insertion of the heart valve prosthesis at the site of implantation, that the volume of the collapsed, unexpanded heart valve prosthesis can be kept extremely low, since the volume of the sealing material is largely saved because the terminating material assumes only a fraction of the volume used by conventional sealing materials. The reduction of the volume of the heart valve prosthesis that is to be inserted is one of the key challenges in the development of an artificial heart valve, and the present proposal provides an elegant solution approach to this problem.

In accordance with a preferred embodiment of the invention, provision is made so that the terminating material, preferably in the form of a fibre material, includes at least one of the following materials or is formed by at least one of the following materials: a polymer, a biological polymer, an artificial polymer, a cationic polymer, a polycation, in particular of biological origin, chitosan, chitosan chloride, or chitin.

Here, polycationic surfaces which are based on compounds (mixtures or also blends) with diethylaminoethyl dextran or diethylaminoethylated cellulose or which are directly produced by diethylaminoethylation of hydroxyl-rich polymer surfaces are of particular interest. Suitable cationic polymers of synthetic origin can be selected from the group consisting of or comprising reaction products from dimethylamine polyamine epichlorohydrin, polydimethyl-diallyl ammonium chloride, and quaternary derivatives of polydimethylaminoethyl methacrylate.

A material which enables the active production of said thrombus as a result of its surface properties, regardless of an anticoagulation medication, and mechanically stabilises and/or immobilises said thrombus by suitable morphological development is preferably selected for the terminating material. This has the particular advantage that the intended thrombus development is successful in sealing off paravalvular leaks in spite of routinely administered anticoagulation medication, such that a heart valve prosthesis having minimal volume and integrated device for sealing off paravalvular leaks is provided which does not require any modifications or particular adjustment of normal medication. This is preferably achieved by a cationic polymer and/or a polycation and more preferably by chitosan.

In accordance with a preferred embodiment of the invention, provision is also made so that the terminating material is arranged in a blood-permeable bag, which is arranged on an outer side of the main body and is secured to the main body. Here, the bag can be tubular in particular and can run on the outer side of the main body level with the heart valve.

The bag preferably includes a casing in the form of a tissue which has a filter structure with through-openings or pores which have a diameter significantly greater than 10 µm so as to ensure that blood has unhindered access to the terminating material arranged loosely in the bag. If the terminating material is present in the form of fibre material, the diameter of the fibres is preferably greater than the above-mentioned filter structure or the diameter of said through-openings/pores. Due to the polycation effect, the formation of a thrombus in the bag is preferably produced at the terminating material, wherein the surrounding structure spatially delineates the enclosed volume for the polycation or the enclosed thrombus.

In accordance with a preferred embodiment, the bag or casing thereof includes one of the following biocompatible and also chemically and mechanically very stable materials or consists of one of the following materials: polyethylene, more specifically preferably HDPE (high density polyethylene) or UHMWPE (ultra-high-molecular-weight polyethylene) and polyethylene terephthalate (PET). Furthermore, absorbable variants consisting of or comprising polyethylene succinate, polybutylene succinate, polyester, polylactide or polycaprolactone are also suitable.

A further fundamental embodiment of the invention makes provision so that the terminating material is not arranged in an interior surrounded by a casing of a bag, but instead a direct release of the material (in particular polycation fibres or polycation sponge) around the heart valve prosthesis is provided in order to utilise a volume gain by thrombus activation. It is assumed that in the case of implantation the anticoagulant medication is sufficient in any case to avoid an escalation of coagulation cascade and to offer the morphological structure sufficient interactions to immobilise the formed thrombus. In one embodiment the fibres are produced from a compound which is based in part on a rigid polymer matrix and in part on a cationic polymer. The cationic polymer component can be produced here either from a cross-linked variant of an otherwise water-soluble cationic polyelectrolyte, or from a cationic polymer, which is swellable only to a limited extent as a result of moisture. The described compound here advantageously forms different polymer phases, which, under the action of moisture, lead to stresses in the fibre and to a crimping of the fibres.

A further embodiment comprises an option of manufacturing the polycation fibres by electro spinning processes. Thereby, chitosan can spun directly or in mixture with other polymers (preferably PEO—polyethylene oxide) from acidic solution to non woven structures. Already commercially available technical implementations of the electro spinning process allow the execution of the elctrospinning process by spinning several different types of fibres. Moreover, switching to different types of fibres during the electro spinning process can be done. Through such techniques, polycation fibres and a surrounding shell being formed of rigid supporting fibres can be prepared. Such fibers and shell form a part of a preferred embodiment heart valve prosthesis.

In accordance with a further embodiment of the invention, provision is preferably made so that the terminating material, preferably in the form of fibre material, is secured to the main body on an outer side of the main body.

In accordance with a further embodiment of the invention, provision is also made so that the terminating material in the form of fibre material includes multi-filaments each having a plurality of interconnected fibres (or filaments). In one embodiment the fibre material or the multi-filaments or fibres is/are secured to the main body in an integrally bonded, force-fitting and/or form-fitting manner, for example by tying the multi-filaments or fibres to the main body or by gluing the multi-filaments or fibres to the main body. Here, the fibres can be of a different type, for example so as to ensure the mechanical association of the volume in a non-absorbable manner that is stable in the long-term. The fibres can also consist of an absorbable, chitosan-containing or chitosan-based polymer, for example, which assists the thrombus formation in a limited manner over time.

The multi-filaments or fibres thereof preferably have the property that they are mechanically separated by the changing blood flow (i.e. changing with the heartbeat) and thus develop a larger surface and thereby increase the thrombus formation. Multi-filaments also offer the advantage of a high surface alongside small compressed volume. Due to the embodiment as multi-filaments, a quicker, controlled thrombus development is thus supported, whereas the volume as the heart valve prosthesis is introduced at the site of implantation is small. In a further embodiment the multi-filaments are provided with a size before implantation. A size as described herein refers to a coating of the multi-filaments corresponding to an impregnation. Such a size can be applied for example by being sprayed on or by immersion. A size advantageously acts on the multi-filaments in such a way that the multi-filaments can be guided in a compact manner, but smoothly, to the site of implantation and can better separate there quickly in the bloodstream. Suitable sizing agents in principle include biologically compatible polymer coating agents soluble in aqueous medium and preferably polyethylene glycol of various sizes, but preferably in the range of from PEG-400 to PEG-800, polyvinylpyrrolidone, preferably with a K-value ranging from K17 to K30, hyaluronic acid, and polysugar, in particular pullulan or dextrans or mixtures of such compounds. Due to the introduction of a size, it is additionally possible in an improved manner for the thrombus formation to start only at the site of implantation. An optimal insertion of the prosthesis is thus made possible in a reliable manner.

This effect can be positively increased by the combination with, for example, swelling or shrinking segments in the fibre (for example crimping of the fibres). For example, swelling is the production of fibres from a polymer mixture which consists of chitosan and a non-soluble, but biologically safe polymer, such as vinylpyrrolidone co-vinylacetate (P(VP-co-VAc)), or includes such polymers. Proceeding from the fact that the different polymers do not detach from one another reciprocally, a fibre is produced which in the dry state can be straight, but mechanically deforms randomly, for example crinkles, as a result of water absorption. In this case, the matrix of the fibres is formed from a cationic polymer. Water-soluble cationic polymers such as the above-mentioned diethylaminodextran can be converted by admixing a polyanion (for example in the form of 1-20% polyacrylic acid) or by chemical cross-linking (for example by condensation during the melting processing, by reacting with multi-functional isocyanates (preferably hexamethylene diisocyanate (HMDI), epoxy-containing cross-linking agent or by reacting with melamine or derivatives thereof) in the presence of moisture into a stable hydrogel state. In this case the cationic swellable polymer component is suitable for ensuring the thrombus formation. The rigid fibre component can also be formed for example by a bioabsorbable polymer matrix, for example from polycaprolactone or derivatives thereof.

Accordingly, in accordance with an embodiment of the invention, the individual fibres or filaments are designed to deform, in the event of contact with water and/or blood, from an elongate or straight first state into a second state, wherein the fibres in the second state have a multiplicity of curvatures, such that the individual fibres in the second state for example are crimped or wavy. A volume increase of the fibre material is advantageously caused as a result.

In accordance with a corresponding embodiment of the invention, provision is also preferably made so that said fibres include a polymer mixture, wherein the polymer mixture includes chitosan and a polymer not soluble by water and/or blood, preferably P(VP-co-VAc). The use of P(VP-co-VAc) is in particular advantageous because P(VP-co-VAc) demonstrates a hydrogel-like character; this means that (VP-co-VAc) is not soluble in water, but under these conditions remains tacky. In a particular embodiment the polymer mixture can also have a small proportion (up to 10%, preferably up to 5%) of a polyanion, for example polyacrylic acid. The presence of a minimal quantity of a polyanion has the advantage that the polymer mixture can thus be better immobilised by the interaction between polycation and polyanion. In a further embodiment the polymer mixture is formed by chitosan and oxidatively cross-linked polyvinylpyrrolidone. The oxidatively cross-linked polyvinylpyrrolidone is transferred here advantageously in a melting form or from solution into the polymer mixture. In a further embodiment the polymer mixture can be formed from two different polyanions, wherein one of the polyanions is grafted/derivatised with a water-soluble polymer.

As already described above, the release of the fibres of the terminating material can be controlled additionally by a finishing of the fibres, in particular in the form of a coating in the form of a size, with a soluble polymer that behaves in a neutral manner in the biological system and also in particular is biologically degradable. The initiation of the thrombus development can thus be effectively delayed over time. The biologically degradable, soluble polymer can be for example PVP (polyvinylpyrrolidone), PEG (polyethylene glycol), polysugar, in particular pullulan, dextrans, and hyaluronic acid. In a further embodiment the fibres are hydrophobic, whereby diffusion of water/blood is still possible, but is significantly slowed. With this embodiment the fibres are also prevented from sticking to the tube element of the insertion system, which is retracted for release.

In accordance with a further embodiment of the invention, provision is made so that the main body of the prosthesis is configured to be expanded (for example in the known manner by a balloon or by use of a self-expanding material for the main body), in order to expand in particular the heart valve prosthesis at the site of implantation into an intended state.

In accordance with an alternative embodiment of the invention, provision is made so that the main body is self-expandable. Here, the main body is preferably formed from a material which enables an automatic expansion of the main body as soon as this has been released accordingly (for example on account of an elastic, in particular superelastic property of the main body).

The heart valve prosthesis is particularly preferably configured to be implanted by catheter into a body lumen of a patient, preferably by means of TAVI. Accordingly, a further aspect of the invention relates to a system comprising a heart valve prosthesis according to the invention and a catheter device configured for implantation of the heart valve prosthesis.

EXAMPLE 1

Figure 2:
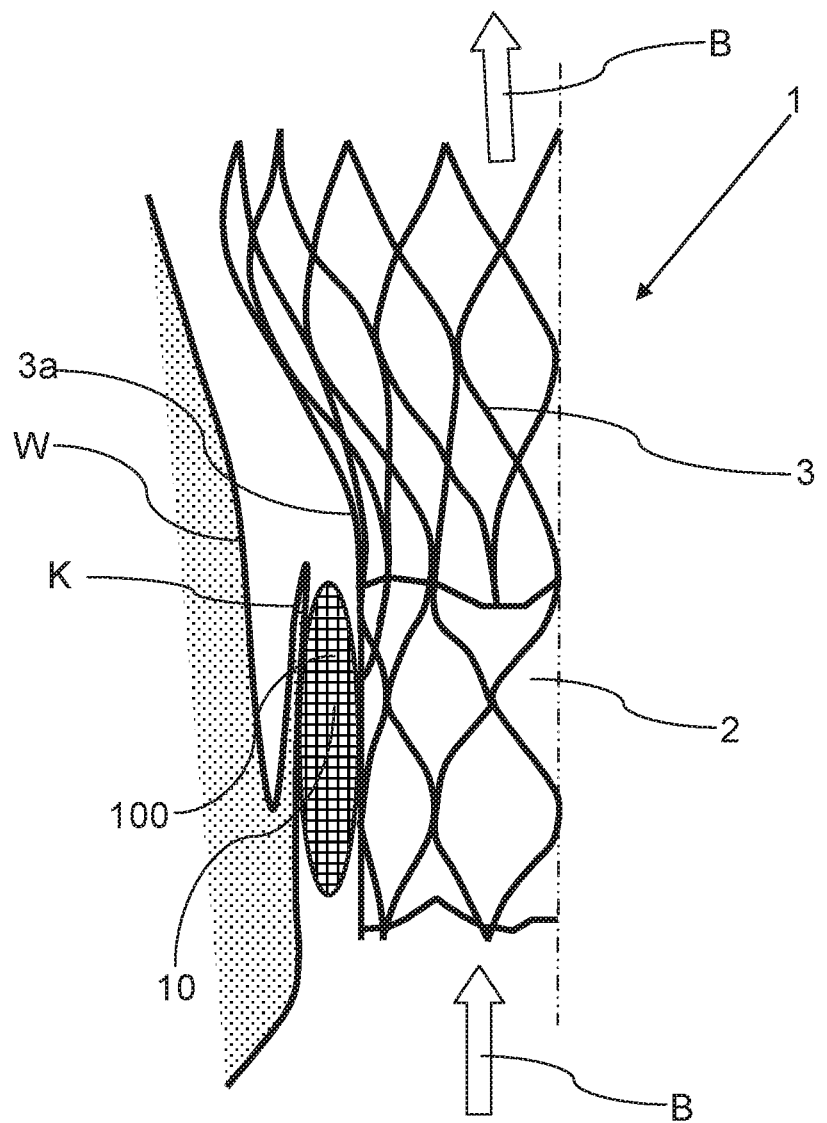
FIG. 2 shows a schematic, partially cutaway view of a detail of the prosthesis according to FIG. 1.

According to FIGS. 1 and 2 the heart valve prosthesis 1 includes a preferably artificial heart valve 2, preferably made of a biological tissue, and also a main body 3 in the form of an expandable or self-expanding stent (see also above), which is configured to accommodate the heart valve in an interior surrounded by the main body, wherein the heart valve 2 is secured to the main body 3, for example by sewing the heart valve 2 to the main body 3.

In the implanted, expanded state, the heart valve prosthesis can be configured for example to displace and functionally replace a defective aortic valve K of a patient. The blood then flows in the direction B through the replacement heart valve 2 secured to the expanded main body, wherein the prosthesis 1 should bear peripherally in a sealing manner against the defective valve K or against the peripheral vessel wall W. Here, there should be no blood flow in particular between the vessel wall W or valve K and the prosthesis 1. Any such blood flow constitutes what is known as a paravalvular leak.

The heart valve prosthesis 1 in accordance with the invention now includes a terminating material 10 on an outer side 3a of the main body 3 facing away from the interior of the main body in order to seal off any such paravalvular leaks, which terminating material is designed, in the event of contact with the blood of a patient in which the heart valve prosthesis 1 has been implanted, to produce a thrombus, which in an ideal case seals off the paravalvular leak. Here, provision is made in accordance with FIGS. 1 and 2 so that the terminating material 10 is arranged in a blood-permeable bag 100, which is arranged on the outer side 3a of the main body 3 and is secured to the main body 3, wherein the bag 100 runs around the main body 3 in the peripheral direction (i.e. transversely to the direction B).

The bag 100 or a casing of the bag 100 enclosing the terminating material 10 can be produced here from a high-strength, approximately inert tissue, preferably from PET. So as not to generate an uncontrolled thrombus formation, the tissue can additionally be provided with an active anticoagulant. The terminating material 10 is disposed within the tissue, for example in the form of textile-immobilised fibres, which trigger a thrombus formation regardless of the presence of coagulants. These fibres for example consist of an insoluble polycation, preferably of chitosan. As a result of active thrombus formation, an inflammatory effect is produced in particular, which promotes tissue build-up around the prosthesis 1. The volume gain produced by the thrombus is intended primarily to permanently close off cavities around the prosthesis 1. If the risk of triggering a coagulation cascade is too high, but also as a preventative measure, the tissue of the bag 100 itself or a local region within the bag 100 can be provided with anticoagulant.

EXAMPLE 2

Figure 3:
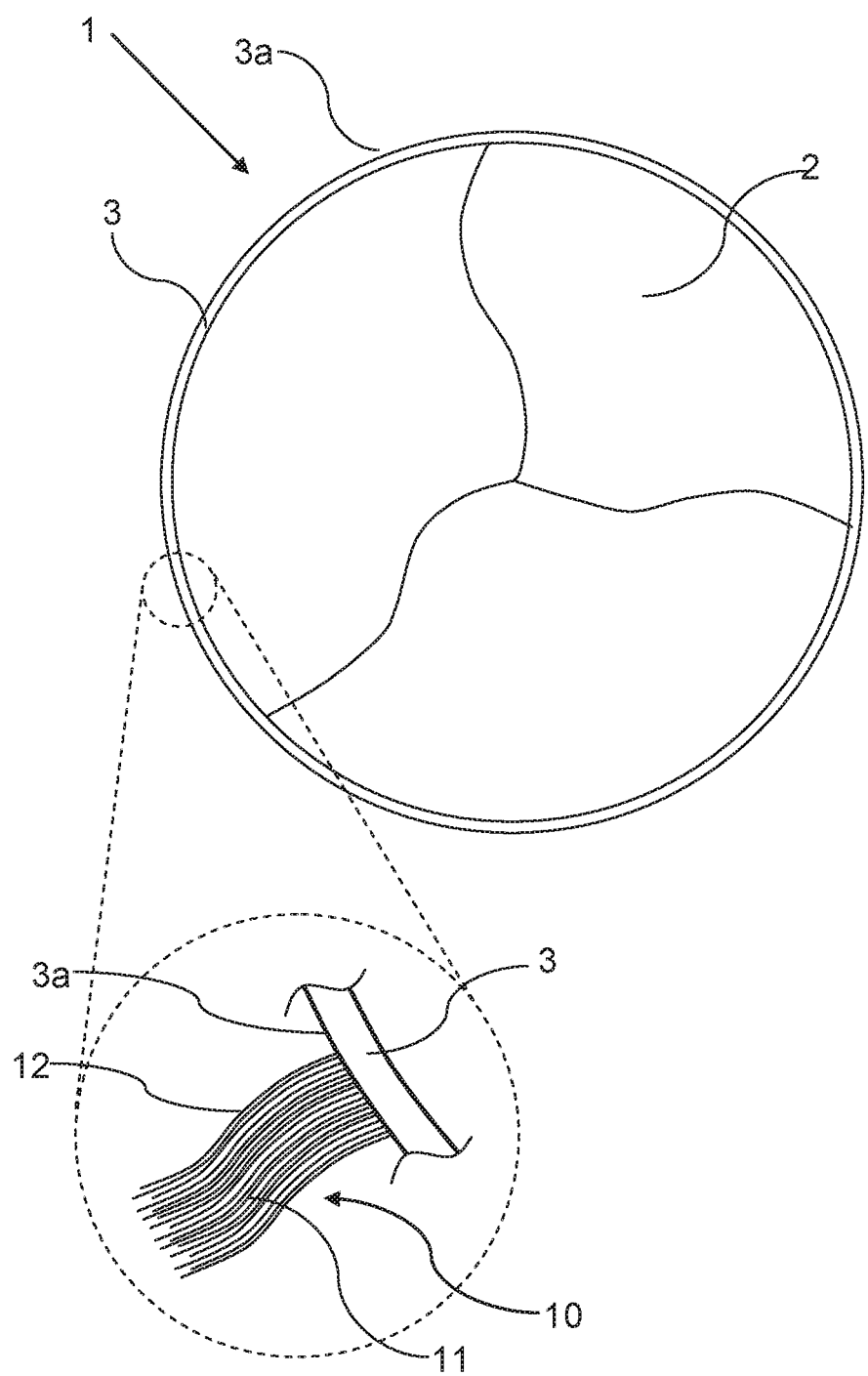
FIG. 3 shows a schematic plan view of a further heart valve prosthesis according to the invention in the embodiment without bag with terminating material in the form of fibre material.

FIG. 3 shows a further embodiment of the invention in which the heart valve prosthesis 1, as described above, includes a main body 3 and also a heart valve 2. In contrast to FIGS. 1 and 2, provision is made here so that the terminating material 10 is secured to the main body, but is not enclosed by a bag 100 delimiting a volume of the thrombus formation.

In accordance with the detail of FIG. 3, the terminating material 10 again includes a plurality of fibres 12, which are secured to the main body 3 on the outer side 3a of the main body 3. Here, provision is preferably made so that the fibres 12 form multi-filaments 11, in each case comprising a multiplicity of interconnected fibres 12.

The multi-filaments, which for example consist of polycation fibres (for example chitosan fibres), are tied to the outer side 3a of the prosthesis 1 or are fixed permanently to the main body 3 via a glued connection or a form-fitting connection.

If these multi-filaments 11 are now exposed to the changing blood flow, they are mechanically separated, thus develop a larger surface, and thereby increase the thrombus formation. This effect can be positively increased by the combination with swelling or shrinking segments in the fibres (for example crimping of the fibres). For example, the production of fibres from a polymer mixture consisting of chitosan and a non-soluble, but biologically safe polymer, such as a P(VP-co-VAc), would be swelling. Accordingly, the fibres 12 in the dry state are straight or elongate, but deform randomly as a result of water absorption.

The release of the fibres 12, preferably by separation of the fibres, can be controlled by providing the fibres 12, for example in the form of a coating of the fibres 12, with a soluble polymer that behaves in a neutral manner in the biological system, and in particular is also biologically degradable (for example PVP, PEG—but preferably polysugars, such as pulluan).

Polysugars, such as pullulan, are used here with preference, since they can be reversibly cross-linked by intensive drying (dehydration) and thus can be tailored in terms of their release function.

As a result, the solutions according to the invention are advantageously suitable for closing off random cavities around the heart valve prosthesis 1 in order to counteract a paravalvular leak.

It will be apparent to those skilled in the art that numerous modifications and variations of the described examples and embodiments are possible in light of the above teaching. The disclosed examples and embodiments may include some or all of the features disclosed herein. Therefore, it is the intent to cover all such modifications and alternate embodiments as may come within the true scope of this invention.

What is claimed is:

1. A heart valve prosthesis, comprising: a main body in the form of an expandable or self-expanding stent; an artificial heart valve secured in the interior of the main body and surrounded by the main body; and a thrombus production and thrombus immobilising terminating material in the form of textile-immobilised fibers within a blood-permeable bag on the outer side of the main body, or a thrombus production and thrombus immobilising terminating material in the form of interconnected multi-filament fibres on the outer side of the main body that mechanically separate from each other in response to blood flow, or a thrombus production and thrombus immobilising terminating material in the form of a permeable sponge-like structure.

2. The heart valve prosthesis according to claim 1, wherein the thrombus production and thrombus immobilising terminating material comprises the textile-immobilised fibers within a blood-permeable bag on the outer side of the main body, wherein the blood-permeable bag comprises liquid permeable material.

3. The heart valve prosthesis according to claim 1, wherein the terminating material comprises at least one of a polymer, a biological polymer, an artificial polymer, a cationic polymer, a polycation, or chitosan.

4. The heart valve prosthesis according to claim 1, wherein the terminating material consists of a polymer, a biological polymer, an artificial polymer, a cationic polymer, a polycation, or chitosan.

5. The heart valve prosthesis according to claim 1, wherein the thrombus production and thrombus immobilising terminating material comprises the textile-immobilised fibers within a blood-permeable bag on the outer side of the main body, wherein the blood-permeable bag comprises at least one of polyethylene, polyethylene terephthalate, polyethylene succinate, polybutylene succinate, polyester, polylactide, and polycaprolactone.

6. The heart valve prosthesis according to claim 1, wherein the thrombus production and thrombus immobilising terminating material comprises the textile-immobilised fibers within a blood-permeable bag on the outer side of the main body, wherein the blood-permeable bag consists of one of polyethylene, polyethylene terephthalate, polyethylene succinate, polybutylene succinate, polyester, polylactide, and polycaprolactone.

7. The heart valve prosthesis according to claim 1, wherein the thrombus production and thrombus immobilising terminating material comprises the interconnected multi-filament fibres on the outer side of the main body, wherein the interconnected multi-filament fibres are secured to the main body in an integrally bonded, force-fitting and/or form-fitting manner.

8. The heart valve prosthesis according to claim 1, wherein the thrombus production and thrombus immobilising terminating material comprises the textile immobilised fibres or the interconnected multi-filament fibres, and the fibres are formed of material to that deforms upon contact with water from an elongate first state into a second state, wherein the fibres in the second state have a multiplicity of curvatures.

9. The heart valve prosthesis according to claim 1, wherein the thrombus production and thrombus immobilising terminating material comprises the textile immobilised fibres or the interconnected multi-filament fibres, and the fibres comprise a polymer mixture, wherein the polymer mixture comprises chitosan and a water-insoluble polymer.

10. The heart valve prosthesis according to claim 9, wherein the water-insoluble polymer comprises P(VP-co-VAc).

11. The heart valve prosthesis according to claim 1, wherein the thrombus production and thrombus immobilising terminating material comprises the textile immobilised fibres or the interconnected multi-filament fibres, and individual fibres of the textile immobilised fibres or the interconnected multi-filament fibres are coated with a soluble polymer.

12. The heart valve prosthesis according to claim 11, wherein the soluble polymer is selected from the group consisting of polyvinylpyrrolidone, polyethylene glycol, hyaluronic acid, and polysugars.

13. The heart valve prosthesis according to claim 11, wherein the soluble polymer comprises polysugars that are selected from pullulan or dextrans.

14. The heart valve prosthesis according to claim 1, wherein the thrombus production and thrombus immobilising terminating material comprises the textile immobilised fibres or the interconnected multi-filament fibres, and the textile immobilised fibres or the interconnected multi-filament fibres comprise polycation fibres and a surrounding shell formed of rigid supporting fibres.

15. The heart valve prosthesis according to claim 1, wherein the heart valve prosthesis is configured to be implanted by a catheter.

16. The heart valve prosthesis according to claim 1, wherein the heart valve is formed of biological tissue.

17. A heart valve prosthesis, comprising a main body in the form of an expandable or self-expanding stent; an artificial heart valve secured in the interior of the main body and surrounded by the main body; and a thrombus production and thrombus immobilising terminating material in the form of textile-immobilised fibers within a blood-permeable bag on the outer side of the main body, or a thrombus production and thrombus immobilising terminating material in the form of interconnected multi-filament fibres on the outer side of the main body that mechanically separate from each other in response to blood flow or a thrombus production and thrombus immobilising terminating material in the form of a permeable sponge-like structure, wherein the terminating material includes at least one of the following materials or is formed by at least one of the following materials: a polymer, a biological polymer, an artificial polymer, a cationic polymer, a polycation, in particular of biological origin, chitosan, chitosan chloride, or chitin.

18. The heart valve prosthesis according to claim 17, wherein the terminating material comprises compounds (mixtures or also blends) with diethylaminoethyl dextran or diethylaminoethylated cellulose or which are directly produced by diethylaminoethylation of hydroxyl-rich polymer surfaces.

19. The heart valve prosthesis according to claim 17, wherein the thrombus production and thrombus immobilising terminating material comprises the textile-immobilised fibers within a blood-permeable bag on the outer side of the main body, wherein the blood-permeable bag comprises or consists of one of the following materials: HDPE (high density polyethylene), UHMWPE (ultra-high-molecular-weight polyethylene), polyethylene terephthalate (PET), polyethylene succinate, polybutylene succinate, polyester, polylactide and polycaprolactone.

20. The heart valve prosthesis according to claim 17, wherein the thrombus production and thrombus immobilising terminating material comprises the interconnected multi-filament fibres on the outer side of the main body, wherein the interconnected multi-filament fibres are secured to the main body in an integrally bonded, force-fitting and/or form-fitting manner.

21. The heart valve prosthesis according to claim 17, wherein the thrombus production and thrombus immobilising terminating material comprises the interconnected multi-filament fibres on the outer side of the main body, wherein the interconnected multi-filament fibres are tied or glued to the main body.

22. The heart valve prosthesis according to claim 17, wherein the thrombus production and thrombus immobilising terminating material comprises the textile immobilised fibres or the interconnected multi-filament fibres, and the textile immobilised fibres or the interconnected multi-filament fibres consist of an absorbable, chitosan-containing or chitosan-based polymer.

23. The heart valve prosthesis according to claim 17, wherein the thrombus production and thrombus immobilising terminating material comprises the interconnected multi-filament fibres on the outer side of the main body, wherein the fibres are secured to the main body in an integrally bonded, force-fitting and/or form-fitting manner.

24. The heart valve prosthesis according to claim 17, wherein the thrombus production and thrombus immobilising terminating material comprises the textile immobilised fibres or the interconnected multi-filament fibres, and individual fibres of the textile immobilised fibres or the interconnected multi-filament fibres are configured and of material to deform upon contact with water from an elongate first state into a second state, wherein the fibres in the second state have a multiplicity of curvatures.

25. The heart valve prosthesis according to claim 17, wherein the thrombus production and thrombus immobilising terminating material comprises the textile immobilised fibres or the interconnected multi-filament fibres, and the fibres of the textile immobilised fibres or the interconnected multi-filament fibres comprise a polymer mixture, wherein the polymer mixture comprises chitosan and a water-insoluble polymer.

26. The heart valve prosthesis according to claim 17, wherein the heart valve is formed of biological tissue.

27. A heart valve prosthesis, comprising a main body in the form of an expandable or self-expanding stent; an artificial heart valve secured in the interior of the main body and surrounded by the main body; and a terminating material on an outer side of the main body formed of material and configured to induce a thrombus, wherein the terminating material includes at least one of the following materials or is formed by at least one of the following materials: a polymer, a biological polymer, an artificial polymer, a cationic polymer, a polycation, in particular of biological origin, chitosan, chitosan chloride, or chitin, wherein the terminating material is arranged in a blood-permeable bag, which is arranged on an outer side of the main body and is secured to the main body at a position of the main body that corresponds to the native heart valve, and wherein the bag comprises a filter structure with through-openings or pores which have a diameter greater than 10 µm and the terminating material is arranged loosely in the bag.

* * * * *